(12) United States Patent
Raestetter et al.

(10) Patent No.: US 7,195,750 B2
(45) Date of Patent: *Mar. 27, 2007

(54) CLINICAL PARAMETERS FOR DETERMINING HEMATOLOGIC TOXICITY PRIOR TO RADIOIMMUNOTHERAPY

(75) Inventors: William Raestetter, Rancho Santa Fe, CA (US); Christine A. White, Rancho Santa Fe, CA (US)

(73) Assignee: Biogen IDEC Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/195,426

(22) Filed: Jul. 16, 2002

(65) Prior Publication Data

US 2003/0211038 A1 Nov. 13, 2003

Related U.S. Application Data

(63) Continuation of application No. 09/625,856, filed on Jul. 26, 2000, now Pat. No. 6,451,284.

(60) Provisional application No. 60/148,288, filed on Aug. 11, 1999.

(51) Int. Cl.
*A61K 51/00* (2006.01)
*A61K 36/14* (2006.01)

(52) U.S. Cl. ............... 424/1.49; 424/1.64; 424/130.1; 424/141.1

(58) Field of Classification Search ............ 424/1.11, 424/1.49, 1.65, 9.1, 9.2, 9.3, 9.4, 9.5, 9.6, 424/9.7, 9.8, 130.1, 131.1, 133.1, 141.1, 424/138.1, 139.1, 155.1; 530/387.1, 387.2, 530/388.1
See application file for complete search history.

(56) References Cited

U.S. PATENT DOCUMENTS

| | | | |
|---|---|---|---|
| 5,124,471 A | 6/1992 | Gansow et al. ............. 558/17 |
| 5,242,679 A * | 9/1993 | Fritzberg et al. ........... 424/1.53 |
| 5,246,692 A | 9/1993 | Gansow et al. ............. 424/1.1 |
| 5,286,850 A | 2/1994 | Gansoh et al. ............. 424/1.45 |
| 5,595,721 A | 1/1997 | Kaminski et al. |
| 5,736,137 A | 4/1998 | Anderson et al. ......... 424/133.1 |
| 5,776,456 A | 7/1998 | Anderson et al. |
| 5,789,554 A | 8/1998 | Leung et al. |
| 5,843,398 A | 12/1998 | Kaminski et al. |
| 5,843,439 A | 12/1998 | Anderson et al. |
| 6,090,365 A | 7/2000 | Kaminski et al. |
| 6,113,898 A | 9/2000 | Anderson et al. |
| 6,183,744 B1 | 2/2001 | Goldenberg |
| 6,306,393 B1 | 10/2001 | Goldenberg |
| 6,451,284 B1 * | 9/2002 | Raestetter et al. ........... 424/9.2 |
| 6,455,043 B1 * | 9/2002 | Grillo-Lopez ............ 424/155.1 |
| 2002/0006404 A1 | 1/2002 | Hanna et al. |
| 2002/0058029 A1 | 5/2002 | Hanna |

FOREIGN PATENT DOCUMENTS

| | | |
|---|---|---|
| WO | WO 92/07466 | 5/1992 |
| WO | WO 98/42378 | 10/1998 |
| WO | WO 00/20864 | 4/2000 |
| WO | WO 00/67796 | 11/2000 |
| WO | WO 00/74718 | 12/2000 |
| WO | WO 01/10461 | 2/2001 |

OTHER PUBLICATIONS

Knox et al, Clinical Cancer Research, 1996, vol. 2, pp. 457-470.*
Eary et al., Imaging and Treatment of B-Cell Lymphoma. *The Journal of Nuclear Medicine*, 31:1257-1268 (Aug. 1990).
Goldenberg et al., Targeting, Dosimetry, and Radioimmunotherapy of B-Cell Lymphomas with Iodine-131-Labeled LL2 Monoclonal Antibody. *The Journal of Clinical Oncology*, 9:548-564 (Apr. 1991).
Hnatowich et al., Patient Biodistribution of Intraperitoneally Administered Yttrium-90-labeled Antibody. *The Journal of Nuclear Medicine* 29:1428-1434 (1988).
Kaminiski et al., Radioimmunotherapy of B-Cell Lymphoma with [131] Anti-B1 (Anti-CD20) Antibody. *The New England Journal of Medicine* 329:459-465 (Aug. 1993).
Press et al., Treatment of Refractory Non-Hodgkin's Lymphoma with Radiolabeled MB-1 (Anti-CD37) Antibody. *Journal of Clinical Oncology* 7:1027-1038 (Aug. 1998).
Press et al., Radiolabeled-Antibody Therapy of B-Cell Lymphoma with Autologous Bone Marrow Support. *The New England Journal of Medicine*, vol. 329 (Oct. 1993).
*Idec Pharmaceuticals v. Corixa Corp.*, Case No. 01-1637-IEG [Doc. Nos. 486, 584] (S.D. Cal. Oct. 14, 2003).
*Biogen Idec v. Corixa Corp.*, Case No. 01-1637-IEG [Doc. Nos. 635, 662, 486] (S.D. Cal. Jan. 22, 2004).
Eary et al., "Imaging and Treatment of B-Cell Lymphona," *J Nucl Med*, 31(8):1257-1268 (1990).

(Continued)

*Primary Examiner*—Dameron L. Jones
(74) *Attorney, Agent, or Firm*—Pillsbury Winthrop Shaw Pittman LLP

(57) ABSTRACT

New clinical parameters are reported which may serve as predictors of the hematological toxicity associated with therapeutic radiolabeled antibodies, particularly those antibodies which target lymphoma cells which have a tendency to localize to the bone marrow.

30 Claims, No Drawings

OTHER PUBLICATIONS

Goldenberg et al., "Targeting, dosimetry, and radioimmunotherapy of B-cell lymphomas with iodine-131-labeled LL2 monoclonal antibody," *J Clin Oncol*, 9(4):548-64 (1991).

Hnatowich et al., "Patient Biodistribution of Intraperitoneally Administered Yttrium-90-labeled Antibody," *J Nucl Med*, 29:1428-35 (1988).

Kaminiski et al., "Radioimmunotherapy of B-Cell Lymphoma with [131] Anti-B1 (Anti-CD20) Antibody," N Engl J Med, 329:459-65 (1993).

Press et al., "Treatment of Refractory Non-Hodgkin's Lymphoma with Radiolabeled MB-1 (Anti-CD37) Antibody", *J Clin Oncol*, 7(8):1027-38 (1989).

Press et al., "Radiolabeled-Antibody Therapy of B-Cell Lymphoma with Autologous Bone Marrow Support," *N Engl J Med*, 329(17):1219-24 (1993).

Maloney et al., "Newer Treatments and Non-Hodgkin's Lymphoma: Monoclonal Antibodies," *Oncology*, 12(8):63-76 (1998) (first page/abstract only).

Behr et al., "Low versus high dose radioimmunotherapy with humanized anti-CD22 or chimeric anti-CD20 antibodies in a broad spectrum of B cell associated malignancies," *Clinical Cancer Research*, 5(10):3304s-3314s (1999).

Wiseman et al., "Radioimmunotherapy of relapsed non-Hodgkin's lymphoma with Zevalin, a 90Y-labeled anti-CD20 monoclonal anitbody," *Clinical Cancer Research*, 5(10):3281s-3286s (1999).

Gopal et al., "Clinical applications of Anti-CD20 antibodies," *J Clin Med*, 134(5):445-450 (1999).

Witzig et al., "Phase I/II trial of IDEC-Y2B8 radioimmunotherapy for treatment of relapsed or refractory CD20(+)B-cell non-Hodgkin's lymphoma," *J Clin Oncol*, 17(12):3793-3803 (1999).

Letter from Ruta Freimanis of the United States Adopted Names Council to John Wood of IDEC Pharmaceuticals dated Sep. 25, 1996.

Wiseman et al., "Zevalin™ Biodistribution and Dosimetry Estimated Normal Organ Absorbed Radiation Doses Are Not Affected By Prior Therapy With Rituximab," Poster presented Dec. 3-7, 1999 (abstract only); Blood, 94(10, Suppl. 1):92a, #403 (1999).

Wiseman et al., "Final Dosimetry Results of IDEC Y2B8 Phase I/II $^{90}$ Yttrium Radioimmunotherapy Trial in Non-Hodgkin's Lymphoma (NHL)," J. Nucl. Med., 40:64P(260) (1999, Jun. Supplement).

Wiseman et al., "IDEC-Y2B8 ($^{90}$ Yttrium Ibritumomab Tiuxetan) Radioimmunotherapy Safey Results in relapsed of Chemotherapy Refractory Non-Hodgkin's Lymphoma (NHL) patients Treated at Reduced Doses Because of Pre-existing Thrombocytopenia," Poster presented Oct. 31-Nov. 4, 1999; Intl. J. Radiation Oncology, 45(3 Suppl):390 (#2217) (1999).

Wiseman et al., "90Yttrium Labeled IDEC Y2B8 Anti-CD20 Radioimmunotherapy of Non-Hodgkin's Lymphoma," Cancer Biotherapy & Radiopharmaceuticals, 14(4):315, abstract #2 (1999).

Leget et al., "Use of rituximab, the new FDA-approved antibody," *Curr Opin Oncol*, 1998, 10(6):548-551.

Matsumura et al., "Establishment and characterization of a new human B-cell line (ONHL-1) from non-Hodgkin's lymphoma: constant expression of bcl-2 gene during mitogen-induced growth inhibition," Int J Cancer, 1990, 46(6):1107-1111 (abstract only).

McLaughlin et al., "Clinical status and optimal use of rituximab for B-cell lymphomas," *Oncology (Huntingt)*, 1998, 12(12):1763-1769.

Wiseman et al., "IDEC-Y2B8 radioimmunotherapy: baseline bone marrow involvement and platelet count are better predictors of hematologic toxicity than dosimetry," Blood, 1998 92(10 Suppl 1): 417a.

White et al., "Radioimmunotherapy of relapsed or refractory non-Hoggkin's lymphoma (NHL): IDEC-Y2B8 phase I/II [90]yttrium trial," Poster presentation at VII International Conference on Malignant Lymphoma, Lugano, Switzerland, *Annals of Oncol*, 1999, 10 (Suppl 3): 64(215).

Kaminski, et al., "Radioimmunotherapy of Advanced B-Cell Lymphoma with Non Bone Marrow Ablative Doses of 131-I MB-1 Antibody," 1990, *Antibody Immunoconjugates, and Radiopharmaceuticals*, vol. 3, No. 1, Abstract No. 83.

Kaminski, et al., "Radioimmunodetection (RID) and Non Marrow Ablative Radioimmunotherapy (RIT) of B-Cell Lymphoma With 131-I MB-1 Antibody," 1990, *Proceedings of ASCO*, vol. 9, p. 271, Abstract No. 1051.

Wahl, et al., "Radioimmunotherapy of B-Cell Lymphoma with I131 MB-1 Monoclonal Antibody," *The Journal of Nuclear Medicine: Proceedings of the 37$^{th}$ Annual Meeting*, p. 852, Abstract No. 622 (1990).

Kaminski, et al., "Phase I Trial Results of 131-I MB-1 Antibody Radioimmunotherapy (RAIT) of B-Cell Lymphoma," 1990, *Antibody Immunoconjugates, and Radiopharmaceuticals*, vol. 4, No. 1, p. 36, Abstract No. 66.

Kaminski, et al., "Phase I Evaluation of 131-I MB-1 Antibody Radioimmunotherapy (RIT) of B-Cell Lymphoma," 1990, *Blood*, vol. 76, No. 10, p. 355a, Abstract No. 1409.

Kaminski, et al., "Imaging, Dosimetry, and Radioimmunotherapy With Iodine 131-Labeled Anti-CD37 Antibody in B-Cell Lymphoma," 1992, *Journal of Clinical Oncology*, vol. 10, No. 11, pp. 1696-1711.

Jensen, et al., "Rapid tumor lysis in a patient with B-cell chronic lymphocytic leukemia and lymphocytosis treated with an anti-CD20 monoclonal antibody (IDEC C2B8, rituximab)," 1998, *Ann Hematol*, vol. 77, pp. 89-91.

Bhagwati et al., 1998, "Fulminant metastatic melanoma complicated by a microangiopathic hemolytic anemia," Hematopathol. Mol. Hematol., 11(2):101-8 (abstract only).

Borden et al., 1999, "Biological therapies for breast carcinoma: concepts for improvement in survival," Semin. Oncol., 26(4 Suppl. 12):28-40 (abstract only).

Byrd et al., 1997, "Leukemic thyrolditis as the initial relapsing sign in a patient with acute lymphocytic leukemia and blast expression of the neural cell adhesion molecule," Am. J. Hematol., 55(4):212-5 (abstract only).

Chang et al, 1999, "Five different anti-prostate-specific membrane antigen (PSMA) antibodies confirm PSMA expression in tumor-associated neovasculature," Cancer Res., 59(13):3192-8 (abstract only).

Chee et al., 1982, "Mouse monoclonal antibody to a melanoma-carcinoma-associated antigen synthesized by a human melanoma cell line propagated in serum-free medium," Cancer Res., 42(8):3142-7 (abstract only).

Crotty et al., 1998, "Morphologic, Immunophenotypic, and molecular evaluation of bone marrow involvement in non-Hodgkin's lymphoma," Diagn. Mol. Pathol., 7(2)90-5 (abstract only).

Larson et al., 1987, "Lymphoma, melanoma, colon cancer: diagnosis and treatment with radiolabeled monoclonal antibodies," The 1986 Eugene P. Pendergrass New Horizons Lecture, Radiology, 165(2):297-304 (abstract only).

Liao et al., 1985, "Monoclonal antibody recognizing human melanoma-carcinoma cross-reacting oncofetal antigen epitopically associated with carcinoembryonic antigen," J. Natl. Cancer Inst, 74(5):1047-1058 (abstract only).

Ojl et al., 1999, "Successful treatment of relapsed T-Cell non-Hodgkin's lymphoma with allogeneic peripheral blood stem cell transplantation with double conditioning," Int. J. Hematol., 69(4):263-7 (abstract only).

Plank et al., 1999, "Primary hepatosplenic T-cell (gamma delta) lymphoma: morphology and immunohistochemistry in cases)," Cesk. Patol., 35(2):55-62 (abstract only).

Putz et al., 1999, "Phenotypic characteristics of cell lines derived from disseminated cancer cells in bone marrow of patients with solid epithelial tumors: establishment of working models for human micrometastasses," Cancer Res., 59(1):241-8 (abstract only).

Rieker et al., 1994, "Disseminated bone marrow metasteses from primary breast cancer. detection and follow-up by radioimmune bone marrow scintigrapy," J. Nucl. Med., 35(9):1485-7 (abstract only).

Ringden et al., 1994, "Long-term follow-up of a randomized trial comparing T cell depletion with a combination of methotrexate and cyclosporine in adult leukemic marrow transplant recipients," Transplantation , 58(8):887-91 (abstract only).

Sao et al., 1999, "A new marrow T cell depletion method using anti-CD6 monoclonal antibody-conjugated magnetic beads and its clinical application for prevention of acute graft-vs-host disease in allogeneic bone marrow transplantation: results of a phase I-II trial," Int. J. Hematol. 69(1):27-35 (abstract only).

Weiner et al., 1999, "An overview of monoclonal antibody therapy of cancer," Semin. Oncol., 26(4 Suppl. 12):41-50.

Wittchow et al., 1992, "Paranuclear blue inclusions in metastatic undifferentiated small cell carcinoma in the bone marrow," Mod. Pathol., 5(5):555-8 (abstract only).

Zhang et al., 1998, "Expression of potential target antigens for immunotherapy on primary and metastatic prostate cancers," Clin. Cancer Res., 4(2):295-302 (abstract only).

Zhang et al., 1998, "Report of 18 cases lymphoblastic lymphoma," Zhonghua Xue Ye Xue Za Zhi, 19(11):566-8 (abstract only).

Press, O.W., "Prospects for the management of non-Hodgkin's lymphomas with monoclonal antibodies and Immunoconjugates," Cancer J. Sci. Am.., Jul. 1998 Suppl. 2:S19-26 (Abstract).

Denardo et al., "Increased survival associated with radiolabeled Lym-1 therapy for non-Hodgkin's lymphoma and chronic lymphocytic leukemia," Cancer, Dec. 15, 1997, 80, 12 Suppl. pp. 2706-2711 (Abstract).

Buchsbaum et al., "Experimental radioimmunotherapay," *Med Phys.*, Mar.-Apr. 1993, vol. 20 (2 Pt 2), pp. 551-67 (Abstract).

Fujimori et al., "Dosimetry and radiation dose distribution in tumors for radioimmunotherapy: the effect of tumor size," *Kaku Igaku*, Mar. 1994, vol. 31, No. 3, pp. 241-8 (Abstract).

Howell et al., "Macroscopic dosimetry for radioimmunotherapy: nonuniform activity distributions in solid tumors," *Med Phys.*, Jan.-Feb. 1989; vol. 16, No. 1, pp. 66-74, (Abstract).

Kennel et al., "Treatment of lung tumor colonies with 90Y targeted to blood vessels: comparison with the alpha-particle emitter 213Bi," *Nucl Med Biol.*, Jan. 1999, vol. 26, No. 1, pp. 149-157 (Abstract).

Mulligan et al., "Phase I study of intravenous Lu-labeled CC49 murine monoclonal antibody in patients with advanced adenocarcinoma," *Clin Cancer Res.*, Dec. 1995. vol. 1, No. 12, pp. 1447-1454 (Abstract).

\* cited by examiner

CLINICAL PARAMETERS FOR DETERMINING HEMATOLOGIC TOXICITY PRIOR TO RADIOIMMUNOTHERAPY

CROSS REFERENCE TO RELATED APPLICATIONS

This is a continuation of U.S. patent application Ser. No. 09/625,856 filed Jul. 26, 2000, now U.S. Pat. No. 6,451,284, issued Sep. 17, 2002, and claims priority to U.S. Provisional Patent Application No. 60/148,288, filed Aug. 11, 1999, both of which are incorporated herein by reference.

FIELD OF INVENTION

The present invention reports new clinical parameters for predicting the hematological toxicity which can be expected upon administering a therapeutic radiolabeled anti-CD20 antibody, as well as other therapeutic antibodies which have the potential to target immune cells. The clinical parameters of the present invention are useful alternatives to performing dosimetry trials with gamma-emitting radiolabeled antibodies prior to therapy.

BACKGROUND OF THE INVENTION

The immune system of vertebrates (for example, primates, which include humans, apes, monkeys, etc.) consists of a number of organs and cell types which have evolved to: accurately and specifically recognize foreign microorganisms ("antigen") which invade the vertebrate-host; specifically bind to such foreign microorganisms; and, eliminate/destroy such foreign microorganisms. Lymphocytes, as well as other types of cells, are critical to the immune system. Lymphocytes are produced in the thymus, spleen and bone marrow (adult) and represent about 30% of the total white blood cells present in the circulatory system of humans (adult).

There are two major sub-populations of lymphocytes: T cells and B cells. T cells are responsible for cell mediated immunity, while B cells are responsible for antibody production (humoral immunity). However, T cells and B cells can be considered interdependent—in a typical immune response, T cells are activated when the T cell receptor binds to fragments of an antigen that are bound to major histocompatability complex ("MHC") glycoproteins on the surface of an antigen presenting cell; such activation causes release of biological mediators ("interleukins") which, in essence, stimulate B cells to differentiate and produce antibody ("immunoglobulins") against the antigen.

Each B cell within the host expresses a different antibody on its surface—thus one B cell will express antibody specific for one antigen, while another B cell will express antibody specific for a different antigen. Accordingly, B cells are quite diverse, and this diversity is critical to the immune system. In humans, each B cell can produce an enormous number of antibody molecules (i.e., about $10^7$ to $10^8$). Such antibody production most typically ceases (or substantially decreases) when the foreign antigen has been neutralized. Occasionally, however, proliferation of a particular B cell will continue unabated; such proliferation can result in a cancer referred to as "B cell lymphoma."

T cells and B cells both comprise cell surface proteins which can be utilized as "markers" for differentiation and identification. One such human B cell marker is the human B lymphocyte-restricted differentiation antigen Bp35, referred to as "CD20." CD20 is a B-lymphocyte-restricted differentiation antigen that is expressed during early pre-B-cell development and remains until plasma cell differentiation. It is believed by some that the CD20 molecule may regulate a step in the B-cell activation process which is required for cell cycle initiation and differentiation. Moreover CD20 is usually expressed at very high levels on neoplastic ("tumor") B-cells. The CD20 antigen is appealing for targeted therapy, because it does not shed, modulate, or internalize. Thus, the CD20 surface antigen is an attractive candidate for "targeting" of B cell lymphomas.

In essence, such targeting can be generalized as follows: antibodies specific to the CD20 surface antigen of B cells are, e.g., injected into a patient. These anti-CD20 antibodies specifically bind to the CD20 cell surface antigen of (ostensibly) both normal and malignant B cells; the anti-CD20 antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to, e.g., the neoplastic B cells. Irrespective of the approach, a primary goal is to destroy the tumor: the specific approach can be determined by the particular anti-CD20 antibody which is utilized and, thus, the available approaches to targeting the CD20 antigen can vary considerably.

For example, attempts at such targeting of CD20 surface antigen have been reported. Murine (mouse) monoclonal antibody 1F5 (an anti-CD20 antibody) was reportedly administered by continuous intravenous infusion to B cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-cell Lymphomas," Blood 69/2: 584–591 (1987).

A potential problem with this approach is that non-human monoclonal antibodies (e.g., murine monoclonal antibodies) typically lack human effector functionality, i.e., they are unable to, inter alia, mediate complement dependent lysis or lyse human target cells through antibody dependent cellular toxicity or Fc-receptor mediated phagocytosis. Furthermore, non-human monoclonal antibodies can be recognized by the human host as foreign proteins; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response. Additionally, these "foreign" antibodies can be attacked by the immune system of the host such that they are, in effect, neutralized before they reach their target site.

One approach at compensating for the lack of effector function of murine antibodies is to conjugate such antibodies to a toxin or radiolabel. Lymphocytes and lymphoma cells are inherently sensitive to radiotherapy. Therefore, B cell malignancies are attractive targets for radioimmunotherapy (RIT) for several reasons: the local emission of ionizing radiation of radiolabeled antibodies may kill cells with or without the target antigen (e.g., CD20) in close proximity to antibody bound to the antigen; penetrating radiation, i.e., beta emitters, may obviate the problem of limited access to the antibody in bulky or poly vascularized tumors; and, the total amount of antibody required may be reduced, thereby alleviating the severity of the potential HAMA response. The radionuclide emits radioactive particles which can damage cellular DNA to the point where the cellular repair mechanisms are unable to allow the cell to continue living;

therefore, if the target cells are tumors, the radioactive label beneficially kills the tumor cells. Radiolabeled antibodies, by definition, include the use of a radioactive substance which may require the need for precautions for both the patient (i.e., possible bone marrow transplantation) as well as the health care provider (i.e., the need to exercise a high degree of caution when working with radioactivity).

A number of specific antibodies have now been disclosed for which a radioactive label or toxin has been conjugated to the antibody such that the label or toxin is localized at the tumor site. For example, the above-referenced IF5 antibody has been "labeled" with iodine-131 ($^{131}$I) and was reportedly evaluated for biodistribution in two patients. See Eary, J. F. et al., "Imaging and Treatment of B-Cell Lymphoma" J. Nuc. Med. 31/8:1257–1268 (1990); see also, Press, O. W. et al., "Treatment of Refractory Non-Hodgkin's Lymphoma with Radiolabeled MB-1 (Anti-CD37) Antibody" J. Clin. Onc. 718:1027–1038 (1989) (indication that one patient treated with $^{131}$I-labeled IF5 achieved a "partial response"); Goldenberg, D. M. et al., "Targeting, Dosimetry and Radioimmunotherapy of B-Cell Lymphomas with Iodine-131-Labeled LL2 Monoclonal Antibody" J. Clin. Onc. 9/4: 548–564 (1991) (three of eight patients receiving multiple injections reported to have developed a HAMA response); Appelbaum, F. R. "Radiolabeled Monoclonal Antibodies in the Treatment of Non-Hodgkin's Lymphoma" Hem./Onc. Clinics of N. A. 5/5:1013–1025 (1991) (review article); Press, O. W. et al "Radiolabeled-Antibody Therapy of B-Cell Lymphoma with Autologous Bone Marrow Support." New England Journal of Medicine 329/17: 1219–12223 (1993) (iodine-131 labeled anti-CD20 antibody IF5 and B1); and Kaminski, M. G. et al "Radioimmunotherapy of B-Cell Lymphoma with $^{131}$I Anti-B1 (Anti-CD20) Antibody". NEJM 329/7 (1993) (iodine-131 labeled anti-CD20 antibody B1; see also U.S. Pat. No. 5,843,398 to Kaminski). Toxins (i.e. chemotherapeutic agents such as doxorubicin or mitomycin C) have also been conjugated to antibodies. See, for example, PCT published application WO 92/07466 (published May 14, 1992).

U.S. application Ser. Nos. 08/475,813, 08/475,815 and 08/478,967, herein incorporated by reference, disclose radiolabeled therapeutic antibodies for the targeting and destruction of B cell lymphomas and tumor cells. In particular, the Y2B8 antibody is disclosed, which is an anti-human CD20 murine monoclonal antibody, 2B8, attached to yttrium-[90] ($^{90}$Y) via the bifunctional chelator, MX-DTPA. This radionuclide was selected for therapy for several reasons. The 64 hour half-life of $^{90}$Y is long enough to allow antibody accumulation by the tumor and, unlike e.g. $^{131}$I, it is a pure beta emitter of high energy with no accompanying gamma irradiation in its decay, with a range of 100 to 1000 cell diameters. The minimal amount of penetrating radiation allows for outpatient administration of $^{90}$Y-labeled antibodies. Furthermore, internalization of labeled antibodies is not required for cell killing, and the local emission of ionizing radiation should be lethal for adjacent tumor cells lacking the target antigen.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in application Ser. Nos. 08/475,813, 08/475,815 and 08/478,967 was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

As also reported in copending application Ser. Nos. 08/475,813, 08/475,815 and 08/478,967 administration of the radiolabeled Y2B8 conjugate, as well as unlabeled chimeric anti-CD20 antibody, resulted in significant tumor reduction in mice harboring a B cell lymphoblastic tumor. Moreover, human clinical trials reported therein showed significant B cell depletion in lymphoma patients infused with chimeric anti-CD20 antibody. In fact, chimeric 2B8 has recently been heralded the nation's first FDA-approved anti-cancer monoclonal antibody under the name of Rituximab® (Rituxan® in the U.S. and Mabthera® in the U.K.).

In addition, U.S. application Ser. No. 08/475,813 discloses sequential administration of Rituxan® with yttrium-labeled Y2B8 murine monoclonal antibody. Although the radiolabeled antibody used in this combined therapy is a murine antibody, initial treatment with chimeric anti-CD20 sufficiently depletes the B cell population such that the HAMA response is decreased, thereby facilitating a combined therapeutic and diagnostic regimen. Moreover, it was shown in U.S. application Ser. No. 08/475,813 that a therapeutically effective dosage of the yttrium-labeled anti-CD20 antibody following administration of Rituxan® is sufficient to (a) clear any remaining peripheral blood B cells not cleared by the chimeric anti-CD20 antibody; (b) begin B cell depletion from lymph nodes; or (c) begin B cell depletion from other tissues.

Thus, conjugation of radiolabels to cancer therapeutic antibodies provides a valuable clinical tool which may be used to enhance or supplement the tumor-killing potential of the chimeric antibody. Given the proven efficacy of an anti-CD20 antibody in the treatment of non-Hodgkin's lymphoma, and the known sensitivity of lymphocytes to radioactivity, it would be highly advantageous for such therapeutic antibodies to become commercially available in kit form whereby they may be readily modified with a radiolabel and administered directly to the patient in the clinical setting.

To this end, U.S. application Ser. No. 09/259,337 discloses methods, reagents and kits for accomplishing radiolabeling of antibodies. Such kits are convenient vehicles for placing these reagents in the clinical setting, in a way that they may be easily produced and administered to the patient before significant decay of the radiolabel or significant destruction of the antibody due to the radiolabel occurs. The kits disclosed in application Ser. No. 09/259,337, herein incorporated by reference, overcome many deficiencies of the prior art which deterred the introduction of such convenient means to commercialize this valuable technology.

The slow introduction of radiolabeling kits to the market may have been due to the poor incorporation efficiencies demonstrated by some known labeling protocols, and the subsequent need to column purify the reagent following the radiolabeling procedure. The delay in development of such kits might also in part be due to the previous lack of accessibility to pure commercial radioisotopes which may be used to generate efficiently labeled products absent subsequent purification. Alternatively, perhaps the reason such kits are generally unavailable is the actual lack of antibodies which have been able to achieve either the approval or the efficacy that Rituxan® has achieved for the treatment of lymphoma in human patients.

For instance, as discussed in U.S. Pat. No. 4,636,380, herein incorporated by reference, it has been generally believed in the scientific community that for a radiopharmaceutical to find clinical utility, it must endure a long and tedious separation and purification process. Indeed, injecting unbound radiolabel into the patient would not be desirable. The need for additional purification steps renders the process of radiolabeling antibodies in the clinical setting an impossibility, particularly for doctors who have neither the equipment nor the time to purify their own therapeutics.

Furthermore, radiolabeled proteins may be inherently unstable, particularly those labeled with radiolytic isotopes such as $^{90}Y$, which have the tendency to cause damage to the antibody the longer they are attached to it in close proximity. In turn, such radiolysis causes unreliable efficiency of the therapeutic due to loss of radiolabel and/or reduced binding to the target antigen, and may lead to undesired immune responses directed at denatured protein. Yet without the facilities for labeling and purifying the antibodies on site, clinicians have had no choice but to order therapeutic antibodies already labeled, or have them labeled off site at a related facility and transported in following labeling for administration to the patient. All such manipulations add precious time to the period between labeling and administration, thereby contributing to the instability of the therapeutic, while in effect decreasing the utility of radiolabeling kits in the clinical setting.

Others have claimed to have developed radiolabeling protocols which would be amenable to kit format in that a separate purification step would not be required (Richardson et al. (1987) Optimization and batch production of DTPA-labeled antibody kits for routine use in $^{111}In$ immunoscintography. Nuc. Med. Commun. 8: 347–356; Chinol and Hnatowich (1987) Generator-produced yttrium-[90] for radioimmunotherapy. J. Nucl. Med. 28(9): 1465–1470). However, such protocols were not able to achieve the level of incorporation that the present inventors have achieved using the protocols disclosed herein, which have resulted in incorporation efficiencies of at least 95%. Such a level of incorporation provides the added benefit of increased safety, in that virtually no unbound label will be injected into the patient as a result of low radioincorporation.

The protocols included in the kits of the invention disclosed in U.S. application Ser. No. 09/259,337 allow rapid labeling which may be affected in approximately a half an hour or as little as five minutes depending on the label. Moreover, as discussed above, the kit protocols disclosed in this application have a labeling efficiency of over 95% thereby foregoing the need for further purification. By foregoing the need for further purification, the half-life of the radiolabel and the integrity of the antibody is reserved for the therapeutic purpose for which it is labeled.

However, there still remain some impediments to convenient clinical use of immunotherapeutics radiolabeled with beta-emitting radioisotopes such as $^{90}Y$. Unlike $^{111}In$, $^{90}Y$ cannot be used for imaging purposes due to the lack of gamma radiation associated therewith. Thus, a diagnostic "imaging" radionuclide, such as $^{111}In$, is usually employed for determining the location and relative size of a tumor prior to and/or following administration of therapeutic chimeric or $^{90}Y$-labeled antibody. Additionally, indium-labeled antibody enables dosimetric assessment to be made, which is generally believed to be required before $^{90}Y$-labeled antibodies are used due to their relatively high potency and tendency to be absorbed in the bones.

For instance, U.S. Pat. No. 5,843,398 of Kaminski et al. discloses a method of administering $^{90}Y$-labeled antibodies to a patient having lymphoma, but maintains that dosimetry is required for $^{90}Y$. To effect dosimetry, Kaminski uses a $^{111}In$-labeled antibody prior to administering the $^{90}Y$-labeled antibody, despite acknowledging that some inaccuracy is anticipated due to the different pharmacokinetic characteristics of the radioisotopes. In addition, the Kaminski patent suggests that dose escalation of $^{90}Y$-labeled antibodies may also be performed in a cautious progression to minimize the chances of irreversible toxicities.

This requirement for dosimetric evaluation prior to administration of a therapeutic antibody detracts from the convenience of using immunotherapy to treat patients in the clinical setting, wastes precious time during which the patient could be undergoing treatment which will actually help alleviate the disease, and increases the exposure to radioactivity for both the patient and the doctor. Moreover, by using diagnostic antibodies which target the same cell surface molecule as the therapeutic antibody, more time must be allotted for the diagnostic antibodies to clear the system in order for the therapeutic antibodies to have a clear path to their target on the surface of malignant B cells. It would be helpful to the field of immunotherapeutics and further facilitate the use of such therapeutics in the clinical setting if methods for predicting the toxicity of radiolabeled antibodies for each particular patient were developed which would enable the clinician to forgo the need for dosimetry with diagnostic radiolabeled antibodies.

SUMMARY OF INVENTION

The present invention provides new clinical parameters for assessing the hematological toxicity of radiolabeled antibodies for a particular patient prior to administration. Such clinical parameters are particularly convenient for predicting the toxicity of $^{90}Y$-labeled antibodies, and particularly those which target molecules on the surface of cancerous cells, particularly B cells, and which are used to treat lymphoma or leukemia, such as anti-CD20, anti-CD19 antibodies or anti-CD22 antibodies. The disclosed parameters have surprisingly provided a more accurate prediction of the risk of bone marrow ablation than standard dosimetry, and may be used to measure the need for bone marrow harvest and transplantation prior to immunotherapy.

DETAILED DESCRIPTION OF THE INVENTION

The present invention encompasses methods of predicting the severity of hematologic toxicity which would result from administration of a radiolabeled antibody to a cancer patient, particularly patients having B cell lymphoma, and using such a prediction to deter or decrease such hematological toxicity prior to administering the radiolabeled antibody. For instance, it has been found that two clinical parameters in particular, baseline platelet count and degree of bone marrow involvement, were better predictors of hematological toxicity in non-Hodgkins B cell lymphoma patients than were dosimetry parameters.

The methods of predicting, then deterring, the toxicity of radioimmunotherapeutics disclosed herein may comprise a variety of steps, including: (a) measuring the degree of bone marrow involvement in a baseline biopsy or baseline platelet count; and (b) administering a therapeutically effective amount of unlabeled chimeric or human antibody if said baseline bone marrow involvement is higher than 5% such that said bone marrow involvement is decreased to less than 5%. Recall that U.S. application Ser. No. 08/475,813, herein incorporated by reference, discloses sequential administration of Rituxan® (chimeric anti-CD20 antibody) with yttrium-labeled Y2B8 murine monoclonal antibody, and discloses that the chimeric antibody may be used to deplete the B cell population prior to administration of the radiolabeled antibody, thereby facilitating a combined therapeutic and diagnostic regimen. The present inventors have surprisingly found that such administration of unlabeled antibody prior to radiolabeled antibody is also effective to reduce the bone marrow involvement in patients having elevated levels of cancerous cells in the marrow such that these patients may be better candidates for radioimmunotherapy.

Thus, the depleting antibodies which may be used in the present invention include unlabeled antibodies and preferably unlabeled anti-CD20 antibodies in the context of B cell lymphoma, wherein said anti-CD20 antibody is a human, chimeric or humanized antibody. Preferably, said antibody is a chimeric or human anti-CD20 antibody, and preferably, that chimeric anti-CD20 antibody is Rituximab®. However, antibodies directed to other B cell surface molecules may be used so long as such cell surface molecules are expressed on the surface of malignant cells. In particular, anti-CD19 and anti-CD22 antibodies may also be used.

For depleting B cells in bone marrow prior to administration of the radiolabeled antibody, chimeric anti-CD20 antibody is administered at a dosage of at least 50 mg/m$^2$ at least one time, and more preferably at a dosage of at least 50 mg/m$^2$ weekly for at least two weeks. Most preferred dosages range from about 100 to about 500 mg/m$^2$ weekly for at least two weeks, and particularly include the dosage regimen of about 375 mg/m$^2$ weekly for four weeks.

It may be the case that no prior treatment is necessary to decrease the level of bone marrow involvement upon measuring the clinical parameters described herein. In such cases, the methods of the present invention may be described as improved methods of treating a patient having B cell lymphoma with a therapeutic radiolabeled antibody, where said improvements include: (a) using a baseline bone marrow biopsy and/or baseline platelet counts as indications of hematological toxicity; and (b) administering a therapeutically effective amount of radiolabeled antibody based on the initial percentage of bone marrow involvement or baseline platelet counts. Of course, if the clinical parameters do suggest a level of bone marrow involvement which will lead to hematological toxicity, the improved methods of the present invention may further comprise administering a dosage or dosage regimen of unlabeled antibody before the radiolabeled antibody if the initial percentage of bone marrow involvement suggests that there will be hematologic toxicity, particularly if the level of bone marrow involvement is greater than 5%, more particularly 15%, and most particularly if the level of bone marrow involvement is greater than 25%.

While any antibody which targets a cell surface molecule which is present on the surface of malignant cells may be used to deliver the radioisotope, preferably said radiolabeled antibody binds to a B cell surface molecule. Most preferred is an anti-CD20 antibody, wherein said radiolabeled anti-CD20 antibody is labeled with an alpha- or beta-emitting isotope. Most preferred isotopes are beta-emitting isotopes due to the range and potency of the decay particles. Preferred beta-emitters include $^{90}$Y and $^{131}$I, although $^{90}$Y is preferred over $^{131}$I, which also emits some gamma irradiation. $^{90}$Y also delivers more energy than does $^{131}$I (2.3 MeV versus 0.81 MeV) and has a longer path length (5–10 mm versus 1–2 mm), which is beneficial for the treatment of bulkier disease where antibody binding to cells on the outer edge of a tumor may kill cells within the tumor without being bound to the surface. Other radionuclides suitable for use in the present invention include $^{188}$Re and $^{186}$Re, $^{199}$Au and $^{67}$Cu. U.S. Pat. No. 5,460,785 provides a listing of suitable radioisotopes and is herein incorporated by reference.

A preferred radiolabeled antibody to be used in the present invention is Y2B8, which is a murine anti-CD20 antibody conjugated to $^{90}$Y by a bifunctional chelator. The preparation and use of Y2B8 is disclosed in U.S. application Ser. Nos. 08/475,813, 08/475,815 and 08/478,967 which are herein incorporated by reference. While murine antibodies are generally preferred over chimeric antibodies for administering a radioisotope to a human patient due to their relatively shorter half-life, human, chimeric, domain-deleted or humanized antibodies may also be used as the radioimmunotherapeutic. Such antibodies may require different dosages depending on the conjugated radiolabel and their stability in vivo.

An important goal of the methods of the present invention is to utilize unlabeled tumor cell-targeting antibodies to deplete tumor cells located in the bone marrow of patients seeking to undergo radioimmunotherapy. Thus, a therapeutically effective amount of unlabeled antibody to be used in the disclosed methods is an amount which is effective to decrease bone marrow involvement below a specified level. In particular, the unlabeled antibodies of the present invention are administered if said baseline bone marrow involvement is higher than 15% such that said bone marrow involvement is decreased to less than 15%. More particularly, the unlabeled antibodies of the present invention are administered if said baseline bone marrow involvement is higher than 25% such that said bone marrow involvement is decreased to less than 25%. And most ideally, the unlabeled antibodies of the present invention are administered if said baseline bone marrow involvement is higher than 25% such that said bone marrow involvement is decreased to less than 15%, and most preferably to less than 5%. Actual numeric doses will depend on the sensitivity of the patient, the type of antibody to be used, the antigen being targeted, and the level of bone marrow involvement and baseline platelet counts.

Another goal of the methods of the present invention is to enable treatment of a cancer patient, and particularly patients having B cell lymphoma, with a radiolabeled immunotherapeutic antibody such that prior imaging or classical dosimetry is not required. The clinical parameters disclosed herein may be substituted for such dosimetry evaluations, and are actually better predictors of the hematological toxicity which can be expected upon administering a radiolabeled antibody to a particular patient than are dosimetry estimates performed with indium-[111]-labeled antibodies. Such methods are particularly useful when used in conjunction with the radiolabeling methods and kits disclosed in U.S. application Ser. No. 09/259,337, which facilitate rapid labeling and convenient administration of radiolabeled antibodies without prior purification.

Dosage amounts of radiolabeled antibody will of course depend upon the particular patient, the particular antibody, the particular target, and the particular radiolabel. Also pertinent is the extent of initial bone marrow involvement and the efficacy of the prior treatment with unlabeled depleting antibody. But for $^{90}$Y-labeled anti-CD20 antibody and particularly Y2B8, preferred dosages will range from about 0.1 to 0.5 mCi/kg. Appropriate dosages for any particular antibody may be determined through routine optimization by the skilled practitioner.

The methods of the present invention will benefit patients with any type of cancer which may involve the penetration of malignant cells into the bone marrow, i.e. a lymphoma or leukemic-type cancer, wherein such patients would otherwise benefit from radioimmunotherapy using an antibody which targets a cell surface molecule on the surface of such cancerous cells. The targeted tumor cells may include any cells which have the capability of infiltrating the bone marrow, including T cells and B cells.

One of the underlying observations that makes the methods disclosed herein so useful is that patients having bone marrow involvement are particularly susceptible to radioimmunotherapy when the radiolabeled antibodies are targeting cells in the bone marrow. Radioisotopes in the bone marrow ablate normal progenitor cells which may not even express the targeted cell surface molecule, thereby depleting the population of immune cells which would normally facilitate reconstitution of the immune system following radioimmunotherapy. Moreover, patients who do have bone marrow involvement do not benefit from autologous bone marrow harvest and transplantation, since such transplantation merely reinfuses tumor cells back into the patient. Thus, having a routine method whereby bone marrow involvement is identified and rectified prior to radioimmunotherapy would be a valuable addition to the field of lymphoma treatments. In this regard, the clinical parameters disclosed herein would likely also indicate the extent of bone marrow toxicity experienced by antibodies labeled with other cytotoxic moieties, e.g. toxins. Thus, the parameters disclosed herein may also be used to predict and deter toxicity and bone marrow ablation due to administration of cytotoxic antibodies.

The methods of the present invention may be used to treat a variety of cancers, particularly B cell lymphomas and leukemias, but are particularly useful wherein said B cell lymphoma is non-Hodgkin's lymphoma (NHL). Rituximab® has already been approved for the treatment of low-grade-follicular NHL, but the present inventors have surprisingly found that Rituximab® is also beneficial for the treatment of intermediate- and high-grade NHL, including bulky disease. Accordingly, the lymphomas which are treatable by the methods of the present invention include low grade/follicular non-Hodgkin's lymphoma (NHL), small lymphocytic (SL) NHL, intermediate grade/follicular NHL, intermediate grade diffuse NHL, chronic lymphocytic leukemia (CLL), high grade immunoblastic NHL, high grade lymphoblastic NHL, high grade small noncleaved cell NHL, bulky disease NHL, mantle cell lymphoma, AIDS-related lymphoma and Waldenstrom's Macroglobulinemia, or any type of lymphoma that is potentially accompanied by bone marrow involvement which could complicate the efficacy of radioimmunotherapy.

Exemplary use of the disclosed clinical parameters will now be illustrated by way of the following data.

A phase I/II study was performed with Y2B8 involving fifty-eight relapsed or refractory non-Hodgkins lymphoma (NHL) patients (6% small lymphocytic, 65% follicular, 24% DLC & DMC, 6% mantle cell). All patients underwent imaging and dosimetry with $^{111}$In-labeled antibody (In2B8) (also disclosed in application Ser. Nos. 08/475,813, 08/475,815 and 08/478,967, herein incorporated by reference) one week prior to therapy. Rituximab® 250 mg/m$^2$ was given prior to both imaging and therapeutic radiolabeled antibodies. Treatment was given to 50 Group 2 and 3 patients as outpatient single-dose 0.2, 0.3 or 0.4 mCi/kg. Phase II doses of 0.4 mCi/kg and 0.3 mCi/kg for patients with mild thrombocytopenia (platelets 100–150/mm$^3$) were chosen.

Analysis of bone marrow dosimetry (including whole blood T1/2 and AUC, blood- and sacral-derived bone marrow dosimetry) versus grade hematologic toxicity for Phase II patients receiving 0.4 mCi/kg or 0.3 mCi/kg did not demonstrate a significant correlation. A significant correlation was demonstrated, however, between the degree of bone marrow involvement with lymphoma and incidence of Grade 4 nadir (platelets $\leq$25,000/mm$^3$; ANC$\leq$500/mm$^3$). Eight percent (2/25) of patients without bone marrow involvement developed Grade 4 thrombocytopenia versus 25% (1/4) of those with 0.1–5% bone marrow involvement, 45% (5/11) of those with 5–20% involvement and 100% (6/6) of those with 20–25% involvement. Overall, only 5 (10%) of patients developed platelet counts of less than 10,000/mm$^3$.

Mean serum immunoglobulins remained normal over a one-year opposition period. The ORR was 67% (26% CR and 41% PR) in all histologies and at all doses and 82% in low-grade NHL. The median TTP was 12.9+ months for responders, and the duration of the response was 11.7+ months a s predicted by Kaplan-Meier methodology. In patients with baseline splenomegaly, 4/8 (50%) patients responded compared to 74% (29/39) without splenomegaly (p=0.1761).

These results suggest that clinical parameters including baseline platelet count and degree of bone marrow involvement with lymphoma may be able to replace dosimetry for safe administration of Y2B8 and other radiolabeled antibodies in patients and NHL. Hematologic toxicity with Y2B8 is clearly related to therapeutic antibody targeting of lymphoma cells residing in the marrow.

What is claimed:

1. A method for reduction of hernatologic toxicity resulting from administration of a radiolabeled antibody to a cancer patient having bone marrow involvement, the method comprising:
   (a) administering a therapeutically effective amount of non-labeled depleting antibody selected from the group consisting of anti-CD19, anti-CD20 and anti-CD22 antibodies that such that said bone marrow involvement is decreased below the initial degree of bone marrow involvement; and
   (b) administering a therapeutic radiolabeled antibody selected from the group consisting of anti-CD19, anti-CD20 and anti-CD22 antibodies while said bone marrow involvement is decreased below the initial degree of bone marrow involvement;
   said method being performed without prior imaging or dosimetry.

2. The method of claim 1, wherein said cancer patient has lymphoma or leukemia.

3. The method of claim 1, wherein the degree of bone marrow involvement is determined using a baseline biopsy or a baseline platelet count.

4. The method of claim 1, wherein said non-labeled, depleting antibody is a human, chimeric, domain-deleted or humanized antibody.

5. The method of claim 4 wherein said non-labeled, depleting antibody is an anti-CD20 antibody.

6. The method of claim 5, wherein said anti-CD20 antibody is rituxirnab.

7. The method of claim 5, wherein said anti-CD20 antibody is administered at a dosage of at least 50 mg/m$^2$ at least one time.

8. The method of claim 7, wherein said anti-CD20 antibody is administered at a dosage of at least 50 mg/m$^2$ weekly for at least two weeks.

9. The method of claim 8, wherein said anti-CD20 antibody is administered at a dosage of about 100 to about 500 mg/m² weekly for at least two weeks.

10. The method of claim 9, wherein said chimeric anti-CD20 antibody is administered at a dosage of about 375 mg/m² weekly for four weeks.

11. The method of claim 1, wherein the initial percentage of bone marrow involvement is greater than 15% and administration of the non-labeled depleting antibody decreases bone marrow involvement below 15%.

12. The method of claim 1. wherein the initial percentage of bone marrow involvement is greater than 15% and administration of the non-labeled depleting antibody decreases bone marrow involvement below 5%.

13. The method of claim 1, wherein the initial percentage of bone marrow involvement is greater than 25% and administration of the non-labeled depleting antibody decreases bone marrow involvement below 25%.

14. The method of claim 1, wherein the initial percentage of bone marrow involvement is greater than 25% and administration of the non-labeled depleting antibody decreases bone marrow involvement below 15%.

15. The method of claim 1, wherein the initial percentage of bone marrow involvement is greater than 25% and administration of the non-labeled depleting antibody decreases bone marrow involvement below 5%.

16. The method of claim 1, wherein said radiolabeled antibody is labeled with an alpha- or beta-emitting isotope.

17. The method of claim 1, wherein said antibody is labeled with $^{90}Y$ or $^{131}I$.

18. The method of claim 1 wherein said radiolabeled antibody is an antb-CD20 antibody.

19. The method of claim 18, wherein said antibody is Y2B8.

20. The method of claim 1, wherein said antibody is provided by, and labeled using materials and instructions from a radiolabeling kit.

21. The method of claim 1, wherein said cancer is selected from the group consisting of low grade/follicular non-Hodgkin's lymphoma (NHL), small lymphocytic (SL) NHL, intermediate grade/follicular NHL, intermediate grade diffuse NHL, chronic lymphocytic leukemia (CLL), high grade immunoblastic NHL, high grade lymphoblastic NHL, high grade small noncleaved cell NHL, bulky disease NHL, mantle cell lymphoma, AIDS-related lymphoma Waldenstrom's Macroglobulinemia and T cell lymphomas and leukemias.

22. The method of claim 4 wherein said non-labeled, depleting antibody is an anti-CD22 antibody.

23. The method of claim 1 wherein said radiolabeled antibody is a radiolabeled anti-CD22 antibody.

24. The method of claim 18, wherein said radiolabeled antibody is an anti-CD20 antibody labeled with $^{90}Y$, and said therapeutically effective amount of radiolabeled antibody is about 0.1 to 0.5 mCi/kg.

25. The method of claim 1, wherein the initial degree of bone marrow involvement is in the range of from 0.1% to 5%.

26. The method of claim 1, wherein the initial degree of bone marrow involvement is greater than 5%.

27. The method of claim 1, wherein the initial degree of bone marrow involvement is greater than 15%.

28. The method of claim 1, wherein the initial degree of bone marrow involvement is greater than 25%.

29. The method of claim 1, wherein the initial degree of bone marrow involvement is greater than 5% and administration of the non-labeled depleting antibody decreases bone marrow involvement below 5%.

30. The method of claim 1, wherein said therapeutic radiolabeled antibody is provided by, and labeled using materials and instructions from a radiolabeling kit.

* * * * *

UNITED STATES PATENT AND TRADEMARK OFFICE
CERTIFICATE OF CORRECTION

PATENT NO.        : 7,195,750 B2
APPLICATION NO.   : 10/195426
DATED             : March 27, 2007
INVENTOR(S)       : William H. Raestetter et al.

It is certified that error appears in the above-identified patent and that said Letters Patent is hereby corrected as shown below:

Claim 1, line 1 (column 10, line 32), replace "hernatologic" with --hermatologic--.

Claim 1, line 5 (column 10, line 36), add --a-- after amount of

Claim 1, line 8 (column 10, line 39), remove "that" after antibodies

Claim 12, line 1 (column 11, line 11), replace "claim 1." with --claim 1,--

Claim 18, line 1 (column 11, line 31), add --,-- after claim 1

Claim 18, line 2 (column 11, line 32), replace "antb-CD20" with --anti-CD20--

Claim 22, line 1 (column 12, line 11), add --,-- after claim 1

Claim 1, line 1 (column 12, line 13), add --,-- after claim 18

Signed and Sealed this

Nineteenth Day of August, 2008

JON W. DUDAS
*Director of the United States Patent and Trademark Office*